United States Patent
Bonrath et al.

(10) Patent No.: US 8,530,707 B2
(45) Date of Patent: Sep. 10, 2013

(54) SELECTIVE HYDROGENATION CATALYST COMPRISING PALLADIUM ON POROUS SILICA GLASS AND THE USE THEREOF

(75) Inventors: Werner Bonrath, Frelburg (DE); Bernd Ondruschka, Leipzig (DE); Christine Schmoeger, Toppeln (DE); Achim Stolle, Jena (DE)

(73) Assignee: DSM IP Assets B.V., Heerlen (NL)

( * ) Notice: Subject to any disclaimer, the term of this patent is extended or adjusted under 35 U.S.C. 154(b) by 46 days.

(21) Appl. No.: 13/059,477

(22) PCT Filed: Aug. 20, 2009

(86) PCT No.: PCT/EP2009/060764
§ 371 (c)(1),
(2), (4) Date: Jun. 15, 2011

(87) PCT Pub. No.: WO2010/020671
PCT Pub. Date: Feb. 25, 2010

(65) Prior Publication Data
US 2011/0237841 A1  Sep. 29, 2011

(30) Foreign Application Priority Data
Aug. 20, 2008  (EP) ..................... 08162689

(51) Int. Cl.
*C07C 29/17* (2006.01)
*B01J 21/08* (2006.01)
*B01J 35/00* (2006.01)

(52) U.S. Cl.
USPC .......................................... 568/875; 502/262

(58) Field of Classification Search
USPC ........................................ 568/875; 502/262
See application file for complete search history.

(56) References Cited

U.S. PATENT DOCUMENTS

| 3,715,404 A | 2/1973 | Lindlar et al. |
| 6,002,047 A | 12/1999 | Jansen et al. |

FOREIGN PATENT DOCUMENTS
WO  2008/060972  5/2008

OTHER PUBLICATIONS

International Search Report for PCT/EP2009/060764, mailed Oct. 6, 2009.
Freitag et al., "Microwave Assisted Synthesis using Catalysts on Controlled Pore Glass Carriers", Optica Applicata, vol. 35, No. 4, Jan. 1, 2005, pp. 745-752, XP009122652.

*Primary Examiner* — Sikarl Witherspoon
(74) *Attorney, Agent, or Firm* — Nixon & Vanderhye P.C.

(57) ABSTRACT

The present invention is directed to a catalyst comprising palladium on a porous Silica glass as carrier, as well as to the use of such catalyst for the selective hydrogenation of alkines to alkenes.

13 Claims, 1 Drawing Sheet

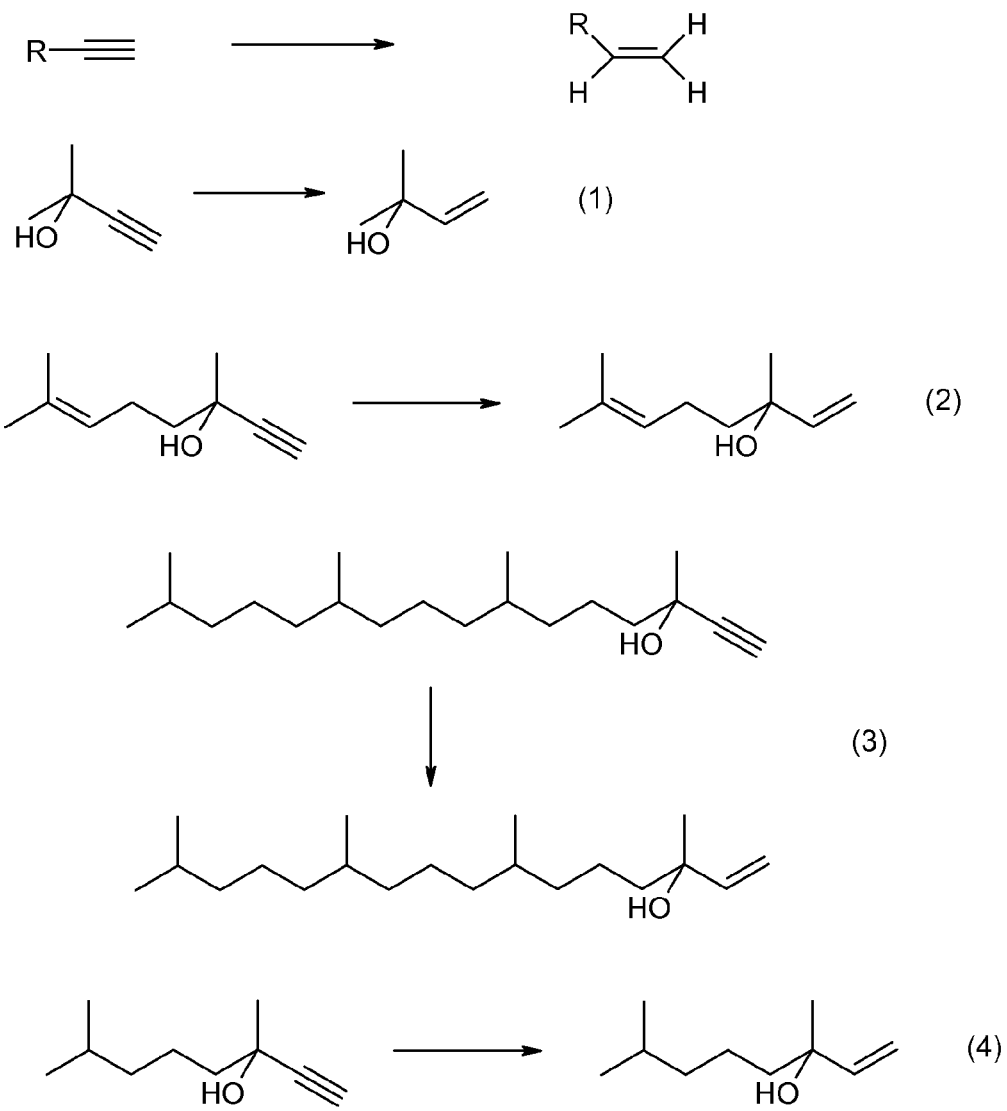

SELECTIVE HYDROGENATION CATALYST COMPRISING PALLADIUM ON POROUS SILICA GLASS AND THE USE THEREOF

This application is the U.S. national phase of International Application No. PCT/EP2009/060764, filed 20 Aug. 2009, which designated the U.S. and claims priority to European Application No. 08162689.7, filed 20 Aug. 2008, the entire contents of each of which are hereby incorporated by reference.

FIELD

The present invention is directed to a catalyst comprising palladium on a porous Silica glass as carrier, as well as to the use of such catalyst for the selective hydrogenation of alkines to alkenes.

BACKGROUND AND SUMMARY

The catalyst of the present invention comprises palladium on a porous Silica glass.

Preferably the catalyst of the present invention is palladium on a porous Silica glass.

The porous Silica glass shows preferably the following characteristics:

a) a particle diameter in the range of 20 to 500 μm, preferably in the range of 50 to 400 μm, more preferably in the range of 80 to 300 μm, most preferably in the range of 100 to 200 μm; and/or b) a pore size in the range of 10 to 400 nm; preferably in the range of 30 250 nm, more preferably in the range of 40 150 nm, most preferably in the range of 50 to 60 nm; and/or c) a pore volume in the range of 100 to 5000 mm$^3$/g; preferably in the range of 250 to 2500 mm$^3$/g, more preferably in the range of 500 to 2000 mm$^3$/g, most preferably in the range of 1000 to 1500 mm$^3$/g; and/or d) a specific surface in the range of 5 to 500 m$^2$/g; preferably in the range of 25 to 300 m$^2$/g, more preferably in the range of 40 to 250 m$^2$/g, most preferably in the range of 50 to 200 m$^2$/g.

Preferably the porous Silica glass shows all characteristics a) to d), whereby the present invention encompasses any possible combination of the preferred/more preferred/most preferred characteristics.

Such porous Silica glasses are commercially available. An especially preferred one is sold under the trademark TRISOPERL® by the Schuller GmbH, Wertheim, Germany. TRISOPERL® is a porous Silica glass with an average particle size in the range of 100 to 200 μm, an average pore size of 54.47 nm, a specific surface of 93.72 m$^2$/g and an average pore volume of 1255.5 mm$^3$/g.

BRIEF DESCRIPTION OF THE DRAWING

FIG. 1 shows the selective catalytic hydrogenation of various alkines to corresponding alkenes that may be accomplished using the catalyst as described herein.

DETAILED DESCRIPTION

The catalyst according to the present invention may be used for the selective hydrogenation of terminal C≡C triple bonds to terminal C═C double bonds in the presence of the following functional groups:

alkyl: linear $C_{1-50}$ alkyl, branched $C_{3-50}$ alkyl, $C_{3-20}$ cycloalkyl, as well as alkylcycloalkyls and cycloalkylalkyls with 1 to 50 C-atoms; preferred are $C_{1-20}$ alkyl—may it be linear ($C_{1-20}$), branched ($C_{3-20}$) or cylic ($C_{3-20}$) or an alkylcycloalkyl ($C_{4-20}$) or a cycloalkylalkyl ($C_{4-20}$);

alkenyl: linear $C_{2-50}$ alkenyl, branched $C_{3-50}$ alkenyl; preferred are $C_{2-20}$ alkenyl—may it be linear ($C_{2-20}$) or branched ($C_{3-20}$);

heteroalkyl: i.e. non-aromatic carbon hydrogen moieties, preferred saturated carbon hydrogen moieties with 3 to 50 C atoms (preferably 3 to 30 C atoms) comprising one or more of the heteroatoms nitrogen and/or oxygen, such as ethers e.g. tetrahydrofuran and tetrahydropyran;

alkylaryl and aryl such as phenyl, tolyl, xylyl, mesityl, naphthyl etc., preferably having 6-17 C atoms;

heteroaryl, preferably having 5-17 C atoms, whereby the heteroatom is either oxygen or nitrogen; the heteroaryl may also contain several heteroatoms (number of heteroatoms≧1), so that also heteroaryl are encompassed which contain O atoms as well as N atoms; examples are pyridyl, indyl, furyl;

hydroxy (—OH);

nitrooxy (—NO$_2$);

amino (—NH$_2$);

SiR$^1$R$^2$R$^3$, wherein R$^1$, R$^2$ and R$^3$ are independently from each other alkyl (linear or branched $C_1$-$C_6$) or aryl or alkylaryl; preferably R$^1$═R$^2$═R$^3$.

That means alkines RC≡CH are hydrogenated to alkenes RHC═CH$_2$, whereby R is a carbon hydrogen moiety optionally bearing a heteroatom O and/or N or several of them and/or the following functional groups as defined above: —OH, —NO$_2$, —NH$_2$, and —SiR$_3$. Preferably R is selected from the group consisting of alkyl, alkenyl, aryl, alkylaryl, heteroaryl,—as defined above—which all may further bear one or more heteroatoms O and/or N, or further functional groups such as —OH, —NO$_2$, —NH$_2$, and —SiR$_3$. Preferably the alkines are precursors of isoprenoid building blocks.

Thus, the present invention is also directed to such use, as well as to a process for the manufacture of alkenes comprising the step of hydrogenating alkines in the presence of a catalyst as defined above.

In general the hydrogenation may be carried out at a temperature in the range of 0° C. to 150° C. and/or at a pressure in the range of 1 bar to 150 bar.

Preferred examples of such alkines and the corresponding alkenes are given in the following table:

| Alkine | Alkene | FIG. 1 |
|---|---|---|
| 2-methylbutinol | 2-methylbutenol | (1) |
| dehydrolinalool | linalool | (2) |
| dehydroisophytol | isophytol | (3) |
| 3,7-dimethyl-1-octyn-3-ol | 3,7-dimethyl-1-octen-3-ol | (4) |

PREFERRED EMBODIMENTS OF THE PRESENT INVENTION

Hydrogenation of Dehydroisophytol to Isophytol

In a preferred embodiment of the present invention the alkine 3,7,11,15-tetramethyl-1-hexadecine-3-ol (dehydroisophytol) is hydrogenated to the alkene 3,7,11,15-tetramethyl-1-hexadecene-3-ol (isophytol).

In general this hydrogenation may be carried out at a temperature in the range of 0° C. to 150° C., preferably at a temperature in the range of 10° C. to 100° C., more preferably at a temperature in the range of 15° C. to 95° C., most preferably at a temperature up to 75° C.

The hydrogen pressure may vary in the range of 1 to 50 bar, preferably in the range of 1.1 to 10 bar, more preferably in the range of 1.2 to 8 bar, most preferably around 6 bar.

Preferably this hydrogenation is performed in the absence of a solvent.

Hydrogenation of 2-methylbutinol to 2-methylbutenol

In another preferred embodiment of the present invention the alkine 2-methylbutinol is hydrogenated to the alkene 2-methylbutenol.

In general this hydrogenation may be carried out at a temperature in the range of 0° C. to 150° C., preferably at a temperature in the range of 15° C. to 80° C., more preferably at a temperature in the range of 20° C. to 75° C., most preferably at a temperature around 60° C.

The hydrogen pressure may vary in the range of 1 to 50 bar, preferably in the range of 1.2 to 15 bar, more preferably in the range of 1.5 to 10 bar, most preferably around 6 bar.

Advantageously a compound poisoning the catalyst, thus reducing its activity, is used. This compound is in general a sulfur- or phosphor containing organic compound. Preferred catalyst poisons are selected from the group consisting of phosphanes (particularly trialklyphosphanes), thioethers, thiols and disulfides. Especially preferred are thioethers such as dipropyl sulfide, ethyl-2-hydroxyethyl sulfide, tetrahydrothiophene, thiophene and 2,2'-(ethylendithio)-diethanol, thiols such as 2,2'-(ethylendioxy)-diethanthiol, and disulfides such as propyl disulfide and isopropyl disulfide. Most preferred is 2,2'-(ethylendithio)-diethanol. The catalyst poison may also be used in the hydrogenation of dehydroisophytol to isophytol as described above.

Hydrogenation of Dehydrolinalool to Linalool

In a further preferred embodiment of the present invention the alkine dehydrolinalool is hydrogenated to the alkene linalool.

In general this hydrogenation may be carried out at a temperature in the range of 0° C. to 120° C., preferably at a temperature in the range of 10° C. to 100° C., more preferably at a temperature in the range of 20° C. to 90° C.

The hydrogen pressure may vary in the range of 1 bar to 50 bar, preferably in the range of 1.2 to 15 bar, more preferably in the range of 1.5 to 10 bar, most preferably around 3 bar.

Hydrogenation of 3,7-dimethyl-1-octyn-3-ol to 3,7-dimethyl-1-octen-3-ol

In another preferred embodiment of the present invention the alkine 3,7-dimethyl-1-octyn-3-ol is hydrogenated to the alkene 3,7-dimethyl-1-octen-3-ol.

The invention will now be illustrated in the following non-limiting examples.

EXAMPLES

The carrier used in the examples was TRISOPERL® sold by the Schuller GmbH, Wertheim, Germany. TRISOPERL® is a porous Silica glass with an average particle size in the range of 100 to 200 μm, an average pore size of 54.47 nm, a specific surface of 93.72 m²/g and an average pore volume of 1255.5 mm³/g.

Example 1

Preparation of the Catalyst 21 mg Pd(OAc)$_2$ (0.09 mmol) were suspended in 50 mL of dichloromethane. 1 g of TRISOPERL® were added and the solvent was removed (bath temperature: 40° C./pressure: 950 mbar). The carrier doped with Pd(OAc)$_2$ was calcinated for 2 hours at 300° C. in an oven (pre-heating of the oven for 20 minutes for 1000 W to 300° C.). The loading of the catalyst on the carrier was then ca. 1 weight-% Pd, i.e. 10 mg Pd on 1 g carrier.

Example 2

Hydrogenation of 2-methyl-3-butin-2-ol (MBI) to 2-methyl-3-buten-2-ol (MBE) in an Autoclave 3.2 mol of MBI were hydrogenated in the presence of 200 mg of the catalyst as prepared according to example 1 at 60° C. and 2.8 bara for 280 minutes under stirring (2000 rpm). The conversion was 98% and the yield 94%.

Examples 3-4

Hydrogenation of Dehydroisophytol (DIP) to Isophytol (IP) without Solvent 3.75 mmol of DIP were hydrogenated in the presence of 100 mg of the catalyst as prepared according to example 1. The temperature and the pressure at which the hydrogenations were carried out are given in the following table. A sample was taken after 3 hours reaction time and the yield and the selectivity determined with gas chromatography.

b) Reaction Time: 3 hours

| Example | Pressure [bara] | Temperature [° C.] | Conversion based on DIP [%] | Selectivity based on IP [%] |
|---|---|---|---|---|
| 3 | 21 | 50 | 88 | 86 |
| 4 | 41 | 50 | 95 | 85 |

Example 5

Solvent Free Hydrogenation of Dehydroisophytol (DIP) to Isophytol (IP) at a Larger Scale 265 g (0.9 mol) of DIP were hydrogenated at 80° C. and 2 bar in the presence of 106 mg of the catalyst as prepared according to example 1 and 23 mg of 2,2'-(ethylendithio)-diethanol in a 500 ml autoclave. The reaction mixture was stirred with 2000 rpm for 4 hours. The conversion was 99% and the yield was 89.6%, based on DIP.

Example 6

Hydrogenation of Dehydroisophytol (DIP) to Isophytol (IP) in a Solvent 3.75 mmol of DIP were dissolved in 0.5 ml of ethyl acetate and hydrogenated at 50° C. and 21 bara in the presence of 100 mg of the catalyst as prepared according to example 1. A sample was taken after 1 hour reaction time and the yield and the selectivity determined with gas chromatography. The conversion was 93% based on DIP and the selectivity 91% based on IP.

The invention claimed is:

1. A method for the selective hydrogenation of C≡C triple bonds to C=C double bonds which comprises subjecting a compound having a C≡C triple bond to hydrogenation conditions in the presence of a catalyst comprising palladium on a porous Silica glass as carrier to yield a compound having a corresponding C=C double bond.

2. The method according to claim 1, wherein the carrier has a particle diameter in the range of 20 to 500 μm.

3. The method according according to claim 1, wherein the carrier has a pore size in the range of 10 to 400 nm.

4. The method according to claim 1, wherein the carrier has a pore volume in the range of 100 to 5000 mm$^3$/g.

5. The method according to claim 1, wherein the carrier has a specific surface in the range of 5 to 500 m$^2$/g.

6. The method according to claim 1, wherein the hydrogenation is carried out in the absence of a solvent.

7. A process for the manufacture of alkenes comprising the step of hydrogenating alkines in the presence of a catalyst comprising palladium on a porous Silica glass as carrier.

8. The process according to claim 7, wherein the alkine is 3,7,11,15-tetramethyl-1-hexadecine-3-ol (dehydroisophytol) and the alkene is 3,7,11,15-tetramethyl-1-hexadecene-3-ol (isophytol).

9. The process according to claim 7, wherein the alkine is 2-methylbutinol and the alkene is 2-methylbutenol.

10. The process according to claim 8, which comprises carrying out the hydrogenation in the presence of a sulfur-containing compound.

11. The process according to claim 10, wherein the sulfur-containing compound is 2,2'-(ethylendithio)-diethanol.

12. The process according to claim 7, wherein the hydrogenation is carried out in the absence of a solvent.

13. The method according to claim 2, wherein the carrier has a particle diameter in the range of 50 to 400 μm.

* * * * *